United States Patent
Kobayashi (10) Patent No.: US 8,397,573 B2
(45) Date of Patent: Mar. 19, 2013

(54) PHOTOACOUSTIC APPARATUS

(75) Inventor: Shuichi Kobayashi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 542 days.

(21) Appl. No.: 12/552,391

(22) Filed: Sep. 2, 2009

(65) Prior Publication Data

US 2010/0058870 A1    Mar. 11, 2010

(30) Foreign Application Priority Data

Sep. 10, 2008  (JP) ................................ 2008-232174

(51) Int. Cl.
*G01N 9/04* (2006.01)

(52) U.S. Cl. ......................................... 73/596; 359/305

(58) Field of Classification Search .................... 73/642, 73/596, 587, 597, 602, 609, 617; 359/305; 356/432

See application file for complete search history.

(56) References Cited

U.S. PATENT DOCUMENTS

| | | | |
|---|---|---|---|
| 3,879,700 A * | 4/1975 | Barkhoudarian et al. ......... 367/7 |
| 4,011,748 A * | 3/1977 | Bond et al. ....................... 73/601 |
| 4,384,231 A * | 5/1983 | Ishikawa et al. ............... 310/335 |
| 4,608,868 A | 9/1986 | Green ............................... 73/606 |
| 5,348,002 A * | 9/1994 | Caro ................................ 600/310 |
| 5,713,356 A * | 2/1998 | Kruger ............................ 600/407 |
| 5,840,023 A * | 11/1998 | Oraevsky et al. ............. 600/407 |
| 6,070,093 A * | 5/2000 | Oosta et al. .................... 600/316 |
| 6,264,610 B1 * | 7/2001 | Zhu ................................ 600/443 |
| 6,309,352 B1 | 10/2001 | Oraevsky et al. ............. 600/407 |
| 7,747,301 B2 * | 6/2010 | Cheng et al. .................. 600/322 |
| 7,917,312 B2 * | 3/2011 | Wang et al. ..................... 702/45 |
| 2005/0070803 A1 * | 3/2005 | Cullum et al. ................. 600/473 |
| 2005/0187471 A1 * | 8/2005 | Kanayama et al. ........... 600/437 |
| 2006/0253007 A1 * | 11/2006 | Cheng et al. .................. 600/310 |
| 2007/0093702 A1 * | 4/2007 | Yu et al. ......................... 600/326 |
| 2007/0187632 A1 | 8/2007 | Igarashi .................... 250/559.36 |
| 2009/0002685 A1 | 1/2009 | Fukutani et al. ................ 356/72 |
| 2009/0138215 A1 * | 5/2009 | Wang et al. ..................... 702/48 |
| 2009/0221911 A1 * | 9/2009 | Igarashi ......................... 600/427 |
| 2009/0312628 A1 * | 12/2009 | Igarashi ......................... 600/425 |

FOREIGN PATENT DOCUMENTS

| | | |
|---|---|---|
| JP | 62-502283 | 9/1987 |
| JP | H03-165257 | 7/1991 |
| JP | 2006-208050 | 8/2006 |
| JP | 2007-216001 | 8/2007 |
| JP | 2008-073341 | 4/2008 |
| JP | 2008-191160 | 8/2008 |
| JP | 2008-307372 | 12/2008 |

OTHER PUBLICATIONS

Office Action issued by JPO on Dec. 11, 2012, in counterpart Japanese patent application 2008-232174, with translation.

* cited by examiner

*Primary Examiner* — Peter Macchiarolo
*Assistant Examiner* — Samir M Shah
(74) *Attorney, Agent, or Firm* — Fitzpatrick, Cella, Harper & Scinto (57) ABSTRACT

A photoacoustic apparatus includes an acoustic lens configured to collect a acoustic wave, an acoustic detector configured to detect the acoustic wave collected by the acoustic lens, a driver configured to move at least one of the acoustic detector and the acoustic lens so as to measure the acoustic wave generated from an object to be measured due to a photoacoustic effect, and a controller configured to output a first measurement signal resulting from the acoustic wave that is generated from a first position in the object, and to eliminate a second measurement signal resulting from the acoustic wave that is generated from a second position different from the first position in the object.

17 Claims, 12 Drawing Sheets

PHOTOACOUSTIC APPARATUS

BACKGROUND OF THE INVENTION

1. Field of the Invention

The present invention relates to an apparatus configured to measure a distribution of a light absorption coefficient in an organism using the photoacoustic effect, and more particularly to an imaging apparatus of an acoustic image formed by the distribution of the light absorption coefficient that is generated by the photoacoustic effect and the array type (acoustic) detector.

2. Description of the Related Art

The photoacoustic method is a method for irradiating excited light onto a sample and for detecting a periodic volume change of the sample that absorbs the light due to the photoacoustic effect. The photoacoustic method enables information of the light absorption distribution in the organism to be measured and visualized.

The near infrared light is light of a wavelength band (700-1200 nm) referred to as an optical window, and has a longer penetration depth in the organism than light having another wavelength band. The near infrared light is less likely to affect the organism than the electromagnetic wave, such as an X ray. Using the near infrared light having such a characteristic, active research on the measurement and visualization of the information in the organism has recently been conducted. The acoustic wave is as safe to the organism as the near infrared light, and can reach a deep portion in the organism. In addition, the acoustic wave characteristically approximately goes straight in the organism different from the near infrared light. Main ingredients of the organism, such as water, fat, oxygenated hemoglobin, reduced hemoglobin, and collagen has a spectrum characteristic to the light of the near infrared region. It is expected that initial symptoms of a disease, such as a cancer, can be observed through a visualization of the space distribution of the ingredients in the organism. However, the organism has a strong scattering characteristic to the near infrared light, and thus it is difficult to obtain spectrum information of a specific site. The spectrum information of the specific site is available with the photoacoustic method that utilizes the characteristics of the acoustic wave and the near infrared light.

There is known a technology to visualize information in the organism using the photoacoustic method (U.S. Pat. No. 5,840,023).

Since the near infrared light strongly scatters in the organism as described above, the light intensity is small in the deep region in the organism. The intensity of the acoustic wave generated from the specific site in the organism is proportional to the light intensity absorbed in that specific site. Therefore, the intensity of the acoustic wave generated in the deep region in the organism is insufficiently small, and the acoustic method of the U.S. Pat. No. 5,840,023 can obtain only a feeble acoustic wave. Similarly, since a ratio of the wavefront of the acoustic wave generated in the deep region in the organism which enters the acoustic detector reduces for a deeper region in the organism, only a feasible acoustic wave can be obtained.

SUMMARY OF THE INVENTION

The present invention provides a photoacoustic apparatus that can obtain light absorption information of a light scatterer, such as an organism, even at a deep position.

A photoacoustic apparatus according to one aspect of the present invention includes an acoustic lens configured to collect a acoustic wave, an acoustic detector configured to detect the acoustic wave collected by the acoustic lens, a driver configured to move at least one of the acoustic detector and the acoustic lens so as to measure the acoustic wave generated from an object to be measured due to a photoacoustic effect, and a controller configured to output a first measurement signal resulting from the acoustic wave that is generated from a first position in the object, and to eliminate a second measurement signal resulting from the acoustic wave that is generated from a second position different from the first position in the object.

Further features of the present invention will become apparent from the following description of exemplary embodiments with reference to the attached drawings.

DESCRIPTION OF THE EMBODIMENTS

A description will be given of a variety of embodiments of the present invention with reference to the accompanying drawings. Those elements in each figure are designated by the same reference numerals, and a duplicate description thereof will be omitted.

First Embodiment

A detailed description will now be given of the visualization technology of the inside of the organism using the photoacoustic method as a comparative example.

Figure 2:
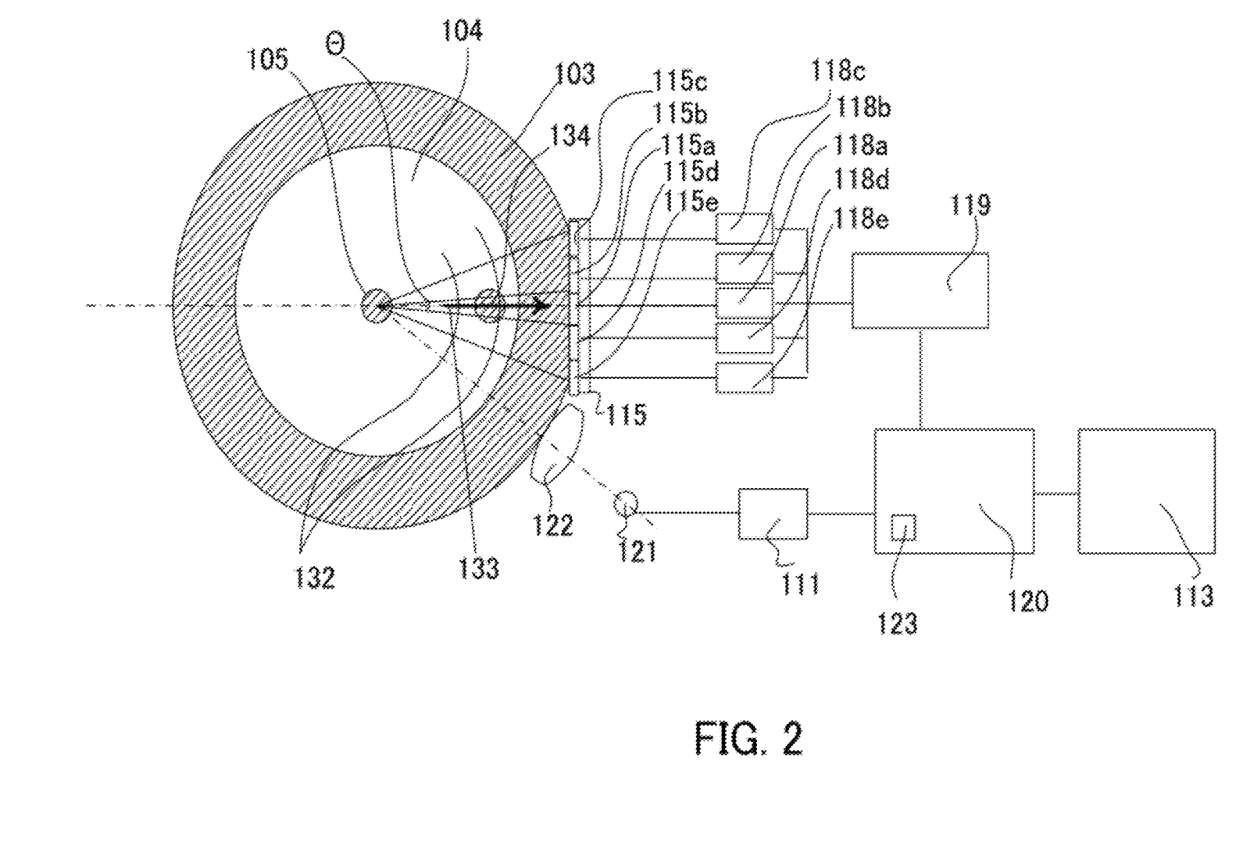
FIG. 2 is a block diagram for explaining a measurement method using a photoacoustic method as a comparative example.

FIG. 2 shows an overview of the photoacoustic method as a comparative example. An object 104 to be measured is an organism, and contains an absorber (first absorbing region) 105 that absorbs the near infrared light and is located at a first position. A matching layer (or matching solution) 103 makes the optical characteristic of the object 104 and that of the near infrared light approximately equal to each other for smooth propagations of the light and acoustic wave. The acoustic wave in this embodiment means an elastic wave that occurs in the object to be measured when the light, such as the near infrared ray, is irradiated onto the object, and the acoustic wave covers a sound wave, an ultrasonic wave, and a photoacoustic wave.

The light source 121 is a light source that irradiates pulsed light of the nanosecond order to the object 104 via an illumination optical system 122. Reference numeral 111 denotes a light source driver configured to drive the light source 121, and connected to a controller 120. The controller 120 has a memory 123. The pulsed light diffuses and propagates in the object 104. The absorber 105 absorbs the diffuse light that has propagated. The absorber 105 abruptly swells due to the absorbed light energy, and consequently generates the acoustic wave in accordance with the size of the absorber 105. The intensity of the acoustic wave is proportional to the light energy absorbed by the absorber.

In FIG. 2, a wavefront 132 is a schematic wavefront of the acoustic wave that has propagated in the direction of an arrow 133. While this embodiment illustrates the acoustic wave generated from the absorber 105, a similar phenomenon occurs in any absorbers in the propagation region of the near infrared light. Therefore, the acoustic wave is generated from a second absorber 134 that is located at a second position in FIG. 2.

The propagating acoustic wave is detected by each array 115a to 115e in an acoustic detector 115 having an array structure, and converted into an electric signal. First acoustic signals (or first measurement signals) from the arrays 115a-115e are reconstructed by the controller 120 via signal converters 118a-118e. The reconstruction can use the conventional "sum and delay" method. The reconstructed image is output as an acoustic image (FIG. 4B) to an output unit 113. The acoustic detector 115 and the signal converters 118a-118e are connected to the controller 120 via an acoustic transducer driver 119.

Figure 3:
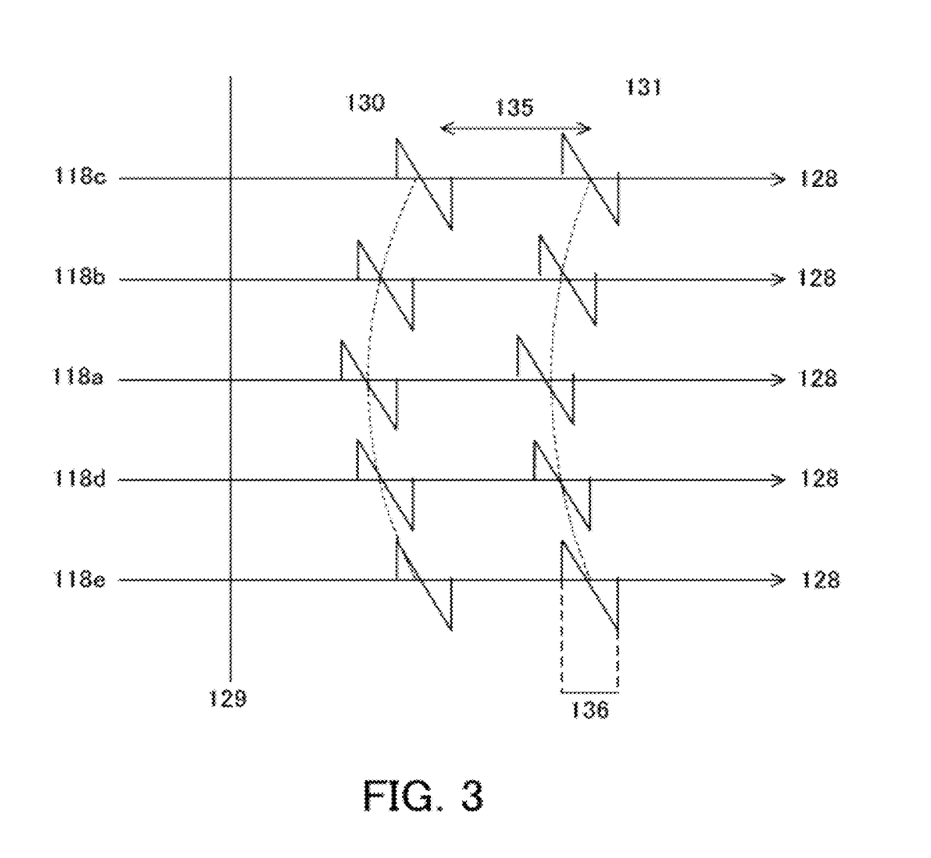
FIG. 3 is a schematic view of an acoustic signal detected and converted into an electric signal by the acoustic detector in the photoacoustic method of the comparative example.

A description will be now given of the signals of the arrays 115a-115e. FIG. 3 is a schematic view of the signal converted by each array part. In FIG. 3, reference numerals 118a-118e denote variations with time of the acoustic waveforms detected by the arrays 115a-115e in the acoustic detector 115 shown in FIG. 2, and each abscissa axis 128 denotes the time. Reference time 129 denotes the time at which the near infrared light is irradiated.

The near infrared light instantly propagates in the organism, and is absorbed by the absorber 105 or second absorber 134 in FIG. 2. The absorber 105 or the second absorber 134 that has absorbed the near infrared light generates the acoustic wave. The acoustic wave propagates in the organism at about 1,500 m/sec. Therefore, the arrays 115a-115e in the acoustic detector 115 detect the acoustic wave with time differences. In FIG. 3, a waveform 130 is a waveform of the acoustic wave generated in the neighboring second absorber 134 in FIG. 2 (and waveform based on the second measurement signal), and a waveform 131 is a waveform of the acoustic wave generated in the absorber 105 (and waveform based on the firs measurement signal).

In these waveforms, delay time 135 is a parameter relating to a distance to the absorber and a period 136 indicates a size of the absorber. By reconstructing these waveforms, information of the absorbers in the organism can be visualized.

As described above, the near infrared light strongly scatters in the organism and the light intensity is small in the organism. Therefore, the intensity of the acoustic wave is feeble when the acoustic wave is generated from the absorber that is located in the deep region in the organism. In addition, the array 115a in the acoustic detector 115 in FIG. 2 can receive a portion corresponding to an angle θ in the wavefront 132 of the acoustic wave generated by the absorber 105, and the detectable acoustic energy is small and a signal from the deep region is unavailable.

Figure 1:
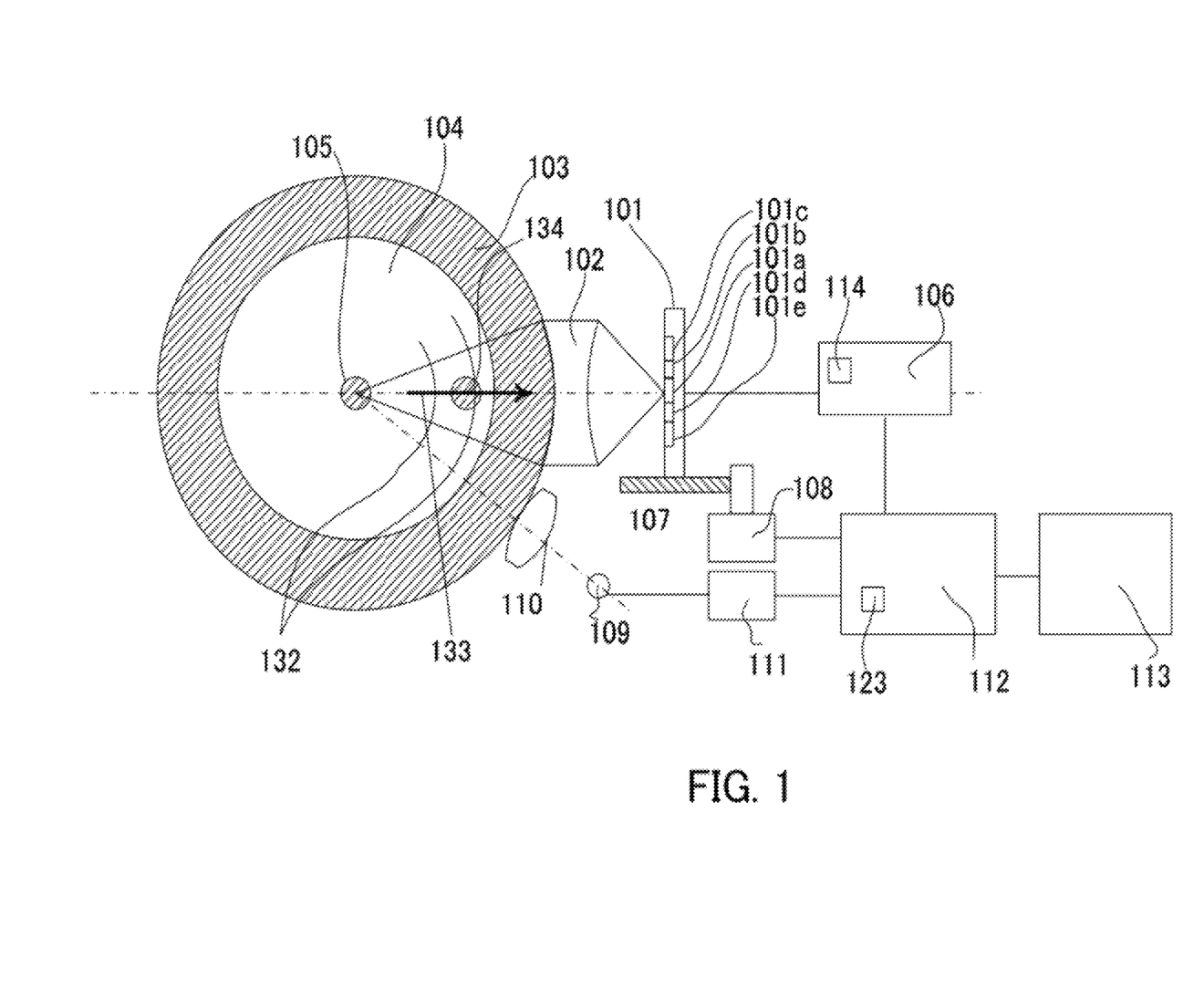
FIG. 1 is a block diagram for explaining a first embodiment of the present invention.

A detailed description of the first embodiment of the present invention. FIG. 1 is a view for explaining a structure according to the first embodiment of the present invention.

In FIG. 1, the object 104 to be measured or examinee is an organism, contains the absorber (first absorbing region) 105 that absorbs the near infrared light and is located at a first position. The matching layer 103 makes the optical characteristic of the object 104 and the optical characteristic of the near infrared light approximately equal to each other for smooth propagations of the light and acoustic wave.

The light source 109 is a light source that irradiates pulsed light of the nanosecond order to the object 104 via an illumination optical system 110. Reference numeral 111 denotes a light source driver configured to drive the light source 109. The pulsed light diffuses and propagates in the object 104, and the absorber 105 absorbs part of the diffuse light. The absorber 105 abruptly swells due to the absorbed light energy, and consequently generates the acoustic wave in accordance with the size of the absorber 105. The intensity of the acoustic wave is proportional to the light energy absorbed by the absorber.

In FIG. 1, a wavefront 132 is a schematic wavefront of the acoustic wave that has propagated in the direction of the arrow 133. While this embodiment illustrates the acoustic wave that is generated from the absorber 105, a similar phenomenon occurs in the absorber in the propagation region of the near infrared light. Therefore, the acoustic wave is generated from a second absorber (second absorbing region) 134, similar to the absorber 105.

The propagating acoustic wave is collected by the acoustic lens 102. In FIG. 1, the absorber 105 and the acoustic detector 101 have a conjugate relationship, and the acoustic wave generated from the absorber 105 is collected by the acoustic detector 101. The condition that the absorber 105 and the acoustic detector 101 have a conjugate relationship is met when their positions are perfectly or substantially conjugate with each other.

The acoustic detector (acoustic transducer) 101 is connected to or provided onto a driver 107, and is configured to move in a direction parallel to an axis of the acoustic lens 102 (which is an optical axis of the lens). The driver 107 is connected to a driver controller 108, and drives the acoustic detector 101 based on a drive signal from the driver controller 108. The driver controller 108 is connected to the controller 112 which, in turn, sends a drive signal to the driver controller 108 based on a signal from the acoustic transducer driver 106 or a preset driving pattern.

In order for the driver 107 to move the acoustic detector 101 in the direction parallel to the axis of the acoustic lens 102, it is sufficient that the moving direction has a component of the axial direction of the acoustic lens 102. In other words, it is not always necessary that the moving direction is parallel to the axial direction.

The driver 107 can move one or both of the acoustic detector (acoustic transducer) 101 and the acoustic lens 102. In moving the acoustic lens, the size of the matching layer may be changed. Both of the acoustic detector (acoustic transducer) 101 and the acoustic lens 102 may be moved without changing their interval or positional relationship. However, the first embodiment advantageously has a simple structure because the acoustic detector (or transducer) 101 is moved in the axial direction of the acoustic lens 102 while the acoustic lens 102 is fixed relative to the object to be measured.

The acoustic detector 101 is connected to the controller 112 via the acoustic transducer driver 106 that includes a signal processor 114 configured to process an acoustic signal (such as the first measurement signal and the second measurement signal) from the acoustic detector 101. The controller 112 has a memory 123, which is configured to store an acoustic image, etc.

A description will now be given of the acquisition principle of the photoacoustic image according to this embodiment.

Figure 4A:
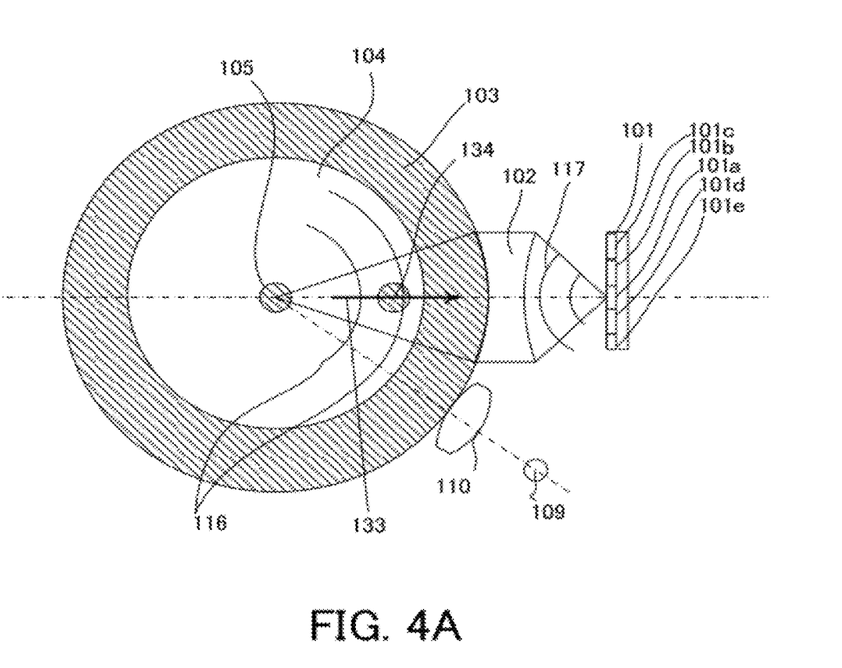
FIG. 4A is a block diagram for explaining a propagation of the acoustic wave when an absorber 105 is conjugate with an acoustic detector 101.

FIG. 4A shows a propagation of the acoustic wave generated in the absorber 105 when the absorber 105 and the array type acoustic detector 101 have a conjugate relationship.

In FIG. 4A, the acoustic wave approximately goes straight in the organism. The wavefront 116 of the acoustic wave generated from the absorber 105 is converted into a convergent wavefront 117 by the acoustic lens 102 and collected on the acoustic detector 101. By this principle, the acoustic image of the absorber 105 is formed on the acoustic detector 101.

Here, assume that L (m) is a distance between the absorber 105 and the acoustic transducer 101 when the size of the absorber 105 is ignored. In addition, assume that v (m/sec) is an acoustic velocity of the acoustic wave that is generated from the absorber 105. Then, the acoustic wave arrives at the acoustic transducer 101 L/v seconds later.

This arrival time interval is determines by a conjugate point or the position of the absorber 105 that is determined by the position of the acoustic transducer 101 and a focal length of the acoustic lens 102.

Hence, the time when the acoustic wave that is generated from the conjugate point arrives at the acoustic transducer can be estimated by measuring a positional relationship between the acoustic transducer 101 and the acoustic lens 102 having a known focal length, and by calculating the conjugate point. Although it is necessary to know the acoustic velocity in the medium but the acoustic velocity in the organism is said to be 1500-1600 m/sec and the time can be calculated with this value. For the precise estimation, it is effective to previously measure the acoustic velocities in the acoustic lens 102 and the matching layer 103 and to use their values.

Figure 4B:
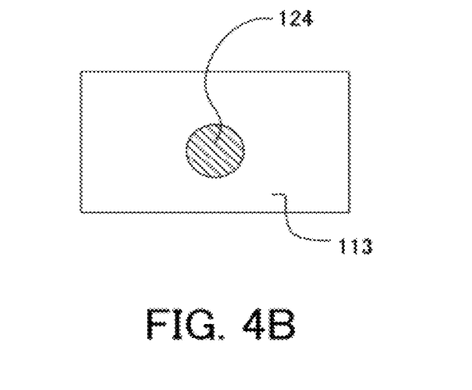
FIG. 4B is a schematic view of a photoacoustic image.

When outputs of the arrays are connected, an image 124 of the absorber 105 shown in FIG. 4B is formed on the image output unit 113.

Figure 5A:
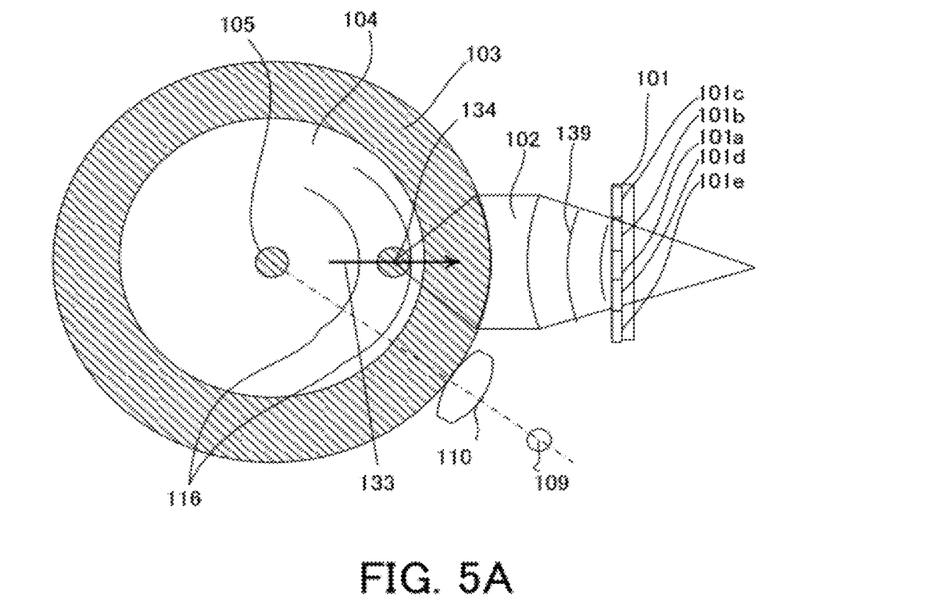
FIG. 5A is a block diagram for explaining a propagation of the acoustic wave when a second absorber 134 is not conjugate with the acoustic detector 101.
Figure 5B:
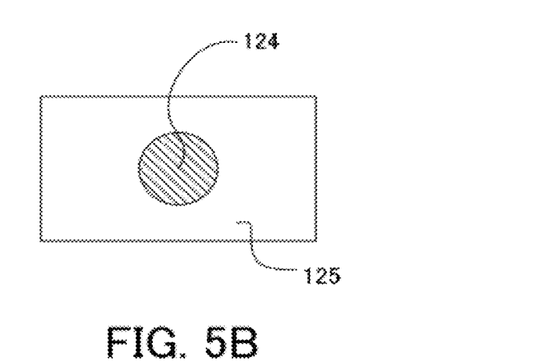
FIG. 5B is a schematic view of a photoacoustic image.

FIG. 5A shows that the acoustic detector 101 and the second absorber 134 have a non-conjugate relationship. The acoustic wave generated from the second absorber 134 is converted into a wavefront 139 by the acoustic lens 102. Since the acoustic detector 101 and the second absorber 134 have a non-conjugate relationship, the wavefront 139 does not focus upon the acoustic detector 101, and thus causes a defocus image. FIG. 5B shows an image of an output unit (not shown) which forms a defocus acoustic image 124 in a background 125.

The defocus acoustic image 124 is formed in a shorter time, because the second absorber 134 is closer to the acoustic transducer 101 than the absorber 105 as the conjugate point. In addition, the formed image is blurred, because there is no conjugate relationship and the acoustic waves that have passed the center and the periphery of the acoustic lens 102 cause a time difference.

Figure 6:
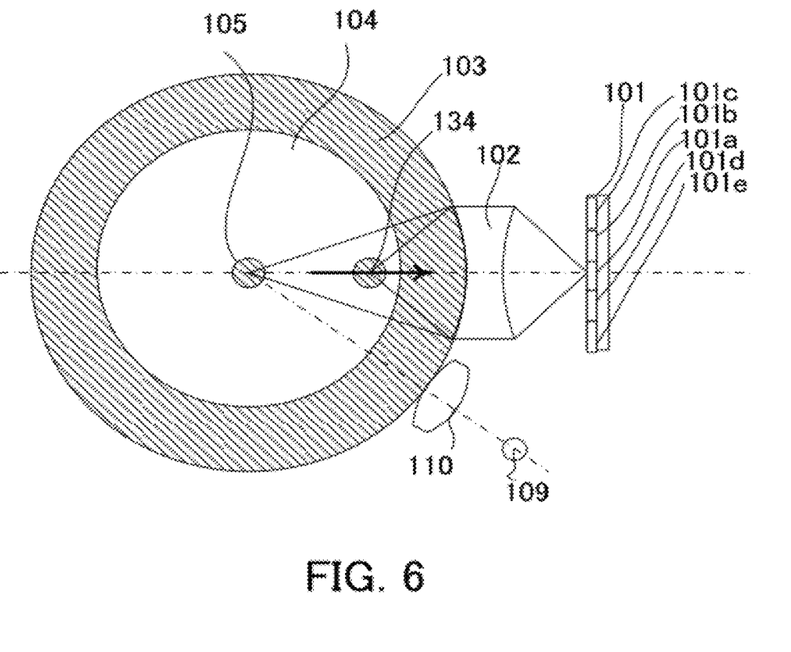
FIG. 6 is a schematic block diagram of the acoustic wave detected by each array part.
Figure 7:
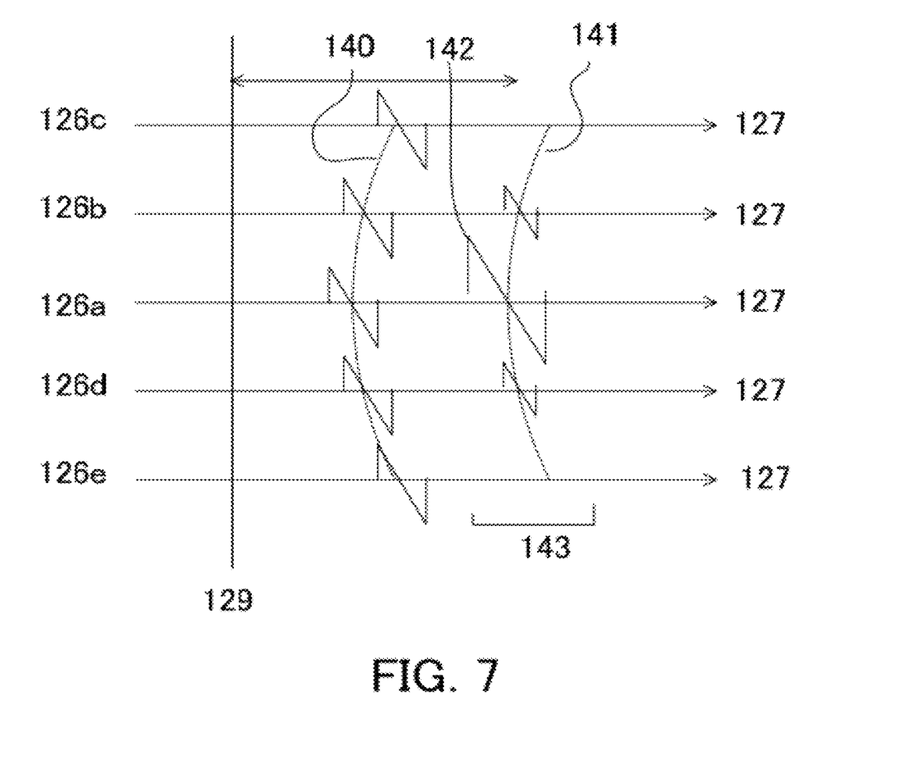
FIG. 7 is a schematic view of an acoustic signal detected and converted into an electric signal by the acoustic detector according to the first embodiment of the present invention.

A description will now be given of the signals of the arrays 101a to 101e. FIG. 6 is a schematic view of the acoustic wave detected by each array. Since the absorber 105 and the second absorber 134 are located at different positions when viewed from the acoustic lens 102 as shown in FIG. 6, each of the arrays 101a to 101e receives the acoustic wave at different time. FIG. 7 schematically shows signals that enter the arrays and are converted by the arrays. Reference numerals 126a-126e denote signals corresponding to the arrays 101a-101e, reference numeral 127 denotes time, and reference numeral 129 denotes reference time.

The second absorber 134 shown in FIG. 6 is close to the acoustic detector 101, and the acoustic signal is observed as the signal 140 shortly after the reference time 129. On the other hand, the absorber 105 is distant from the acoustic detector 101, and the signal from the absorber 105 is detected as a signal (first acoustic wave) 141. Since the absorber 105 has a conjugate relationship with the acoustic detector 101, the signal 126a corresponding to the specific array 101a is more intensely observed.

The acoustic lens 102 enables the acoustic wave near the conjugate point to enter the specific array intensely. Therefore, the acoustic wave generated from a deeper region in the organism can become detected. In particular, this embodiment is effective when the acoustic detector 101 has a limited capability.

In this embodiment, the driver 107 moves the acoustic detector 101 to sequentially obtain the acoustic image, and an image in the depth direction is finally formed.

Thereby, the present invention can efficiently introduce to the acoustic detector 101 the acoustic wave that is generated due to the photoacoustic effect, and form the acoustic image on the acoustic transducer without the reconstruction.

As shown in FIG. 7, the defocus signal (or the second acoustic wave other than the first acoustic wave) 140 is feeble and sometimes becomes a noise. Since the propagation velocity of the acoustic wave in the organism can be roughly calculated, an approximate position of the conjugate point (or conjugate position) can be calculated from the focal length f of the acoustic lens 102 and the position of the acoustic detector 101 (or the positional relationship between the acoustic lens and the acoustic detector). When the photoacoustic detection time is previously estimated from the position of the conjugate point and the signal incident upon at that time is regarded as the acoustic image, the image that is less subject to the noise can be formed.

For example, in FIG. 7, the estimated arrival time 142 of the acoustic image is calculated on the basis of the reference time 129, and the shutter of the acoustic detector 101 is opened in the threshold range 143 that covers the estimated arrival time. The arrival time of the acoustic wave to the acoustic detector 101 is determined by an interval or distance (or positional relationship) between the acoustic detector 101 and the absorber as the acoustic wave source, the propagation velocity of the acoustic wave in the medium between them for transmitting the acoustic wave, etc. Of course, the estimated arrival time (that is an estimation value of the arrival time of the acoustic wave) may be obtained through an operation or a table.

The shutter provided to the acoustic detector 101 on the object side may use a mechanism configured to physically shut the acoustic wave (or to hinder the transmission of the acoustic wave), such as a mechanical shutter, and opening and closing of the shutter may be controlled.

Alternatively, the signal processor 114 may be used which is configured to extract part out of the photoacoustic signal detected and converted by the acoustic detector 101, which part is located in the threshold range 143.

This embodiment uses a process that leaves the (first measurement) signal resulting from the acoustic wave generated from the absorber 105 located at the first position out of the detection result detected by the acoustic detector 101, and that eliminates the (second measurement) signal resulting from the acoustic wave generated from the absorber 134 located at the second position.

One embodiment provides a process that leaves or outputs the (first measurement) signal resulting from the acoustic wave generated from the absorber 105 located at the first position, and that eliminates all other signals. Such a shutter can reduce noises in the acoustic wave detected by the acoustic detector 101 (or prevent the noise from transmitting to the acoustic detector).

When the mechanical shutter opens during a time period that contains the estimated arrival time and closes at the non-estimated arrival time, the acoustic wave that would become a noise can be physically shielded. The signal processor 114 obtains the acoustic signal during a time period that contains the estimated arrival time, and rejects the acoustic signal at the non-estimated arrival time for noise reductions.

The acoustic image can be obtained by spatially connecting the outputs of the arrays measured at this time.

While this embodiment utilizes five illustrative arrays for the acoustic detector 101, an image with a higher resolution is available with more pixels.

In addition, the position of the light source 109 is set, but not limited, to the position shown in FIG. 1 in this embodiment, and a plurality of light sources may be used for similar effects.

As illustrated hitherto, the acoustic image of the conjugate point of the acoustic transducer 101 can be obtained.

A tomogram can be obtained by adjusting an interval between the acoustic lens 102 and the acoustic transducer 101 to move the conjugate point, and by obtaining the conjugate image at that point, after the acoustic image is obtained for one conjugate section.

This embodiment does not reconstruct the signals to obtain an image different from the comparative example, and can make the process system simple.

Precise acoustic imaging can be made by calculating the imaging magnification of the conjugate relationship and by correcting the size of the acoustic image.

Figure 10:
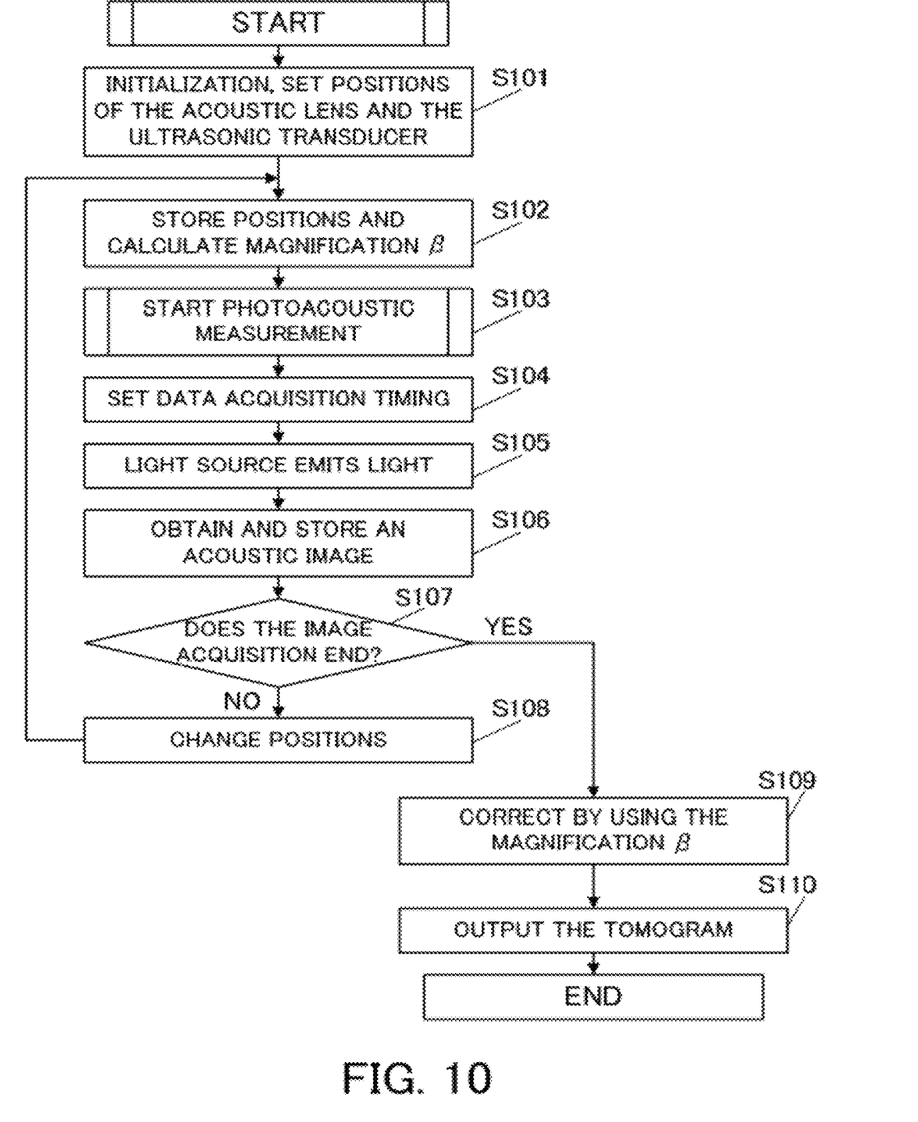
FIG. 10 is a flowchart for obtaining an acoustic image.

FIG. 10 is a flowchart for obtaining the acoustic image.

Initially, a user inputs in an input unit (not shown) a target position in the organism 104 from which the acoustic image is to be obtained, and an image acquisition range to be obtained that includes the target position.

In S101, the controller 112 calculates a position of the acoustic transducer 101 that has a conjugate relationship with the position sought by the user via the acoustic lens 102. Then, the controller 112 moves the acoustic transducer 101 to the conjugate position using the driver 107.

Next, in S102, the positions of the acoustic lens 102 and the acoustic transducer 101 are stored in the memory 123 in the controller 112, and the controller 112 calculates the magnification $\beta$ of the finished image based on the positions.

When a measurement of the photoacoustic image starts in S103, the arrival time necessary for the acoustic wave from the position conjugate with the acoustic transducer 101 is previously estimated in S104 and set to the data acquisition timing.

In S105, the light source driver 111 drives the light source 109 to emit the light. In S106, the acoustic image acquired at the data acquisition timing set in S104 is stored in the memory 123. In S107, the controller 112 determines whether the acoustic image acquisition ends for the entire image acquisition area set by the user.

When the acoustic image acquisition does not end, the flow moves to S108 to change the positions of the acoustic lens 102 and the acoustic transducer 101 and obtain the next acoustic image. Then, S102 to S107 are resumed.

When the acoustic image acquisition ends for the entire image acquisition area set by the user in S107, the flow moves to S109 to correct the acquired tomogram of the organism 104 based on the magnification $\beta$ calculated in S102. In S110, the tomogram corrected by S109 is output to the output unit 113. Next, the image acquisition ends.

This embodiment uses only the near infrared light for the light source to be irradiated into the organism, but the spectral image of the acoustic image can be obtained by changing a wavelength of the light source and by resuming the photoacoustic method. The characteristic of the absorber can be estimated by utilizing the spectral information and recognizing the spectral characteristic of the absorber.

Figure 12:
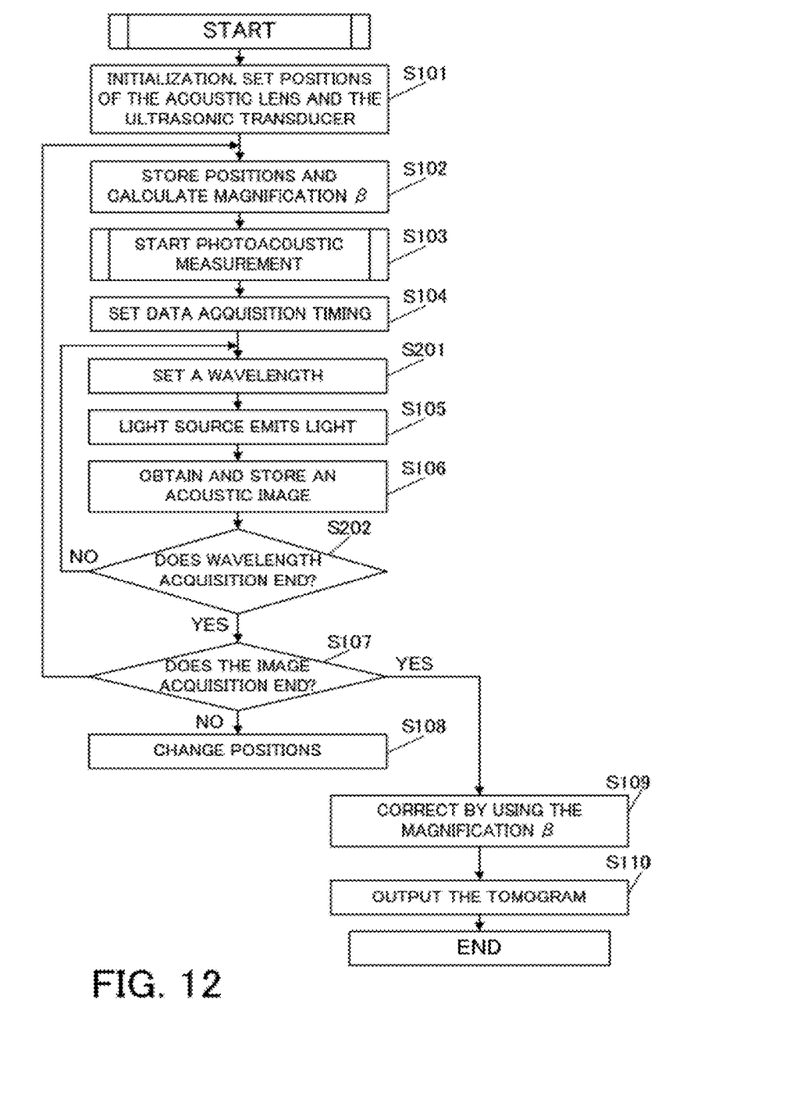
FIG. 12 is a flowchart for obtaining an acoustic image by changing a wavelength of a light source.

FIG. 12 is a flowchart for obtaining the acoustic image by changing a wavelength of the light source.

The flowchart shown in FIG. 12 is different from that of FIG. 10 in that S201 that sets a wavelength of the light source is added between S104 and S105, and S202 that determines whether all acoustic images have been obtained for the target wavelength is added between S106 and S107.

Initially, a user inputs in an input unit (not shown) a target position in the organism 104 from which the acoustic image is to be obtained, an image acquisition range to be obtained that includes the target position, and a type of a wavelength of a light source used to obtain the acoustic image.

In S101, the controller 112 calculates a position of the acoustic transducer 101 that has a conjugate relationship with the position sought by the user via the acoustic lens 102. Then, the controller 112 moves the acoustic transducer 101 to the conjugate position using the driver 107.

Next, in S102, the positions of the acoustic lens 102 and the acoustic transducer 101 are stored in the memory 123 in the controller 112, and the controller 112 calculates the magnification $\beta$ of the image based on the positions.

When a measurement of the photoacoustic image starts in S103, the arrival time necessary for the acoustic wave from the position conjugate with the acoustic transducer 101 is previously estimated in S104, and set to the data acquisition timing.

In S201, the controller 112 sets a wavelength of the light to be irradiated onto the organism 104 from among the wavelength type of the light source input by the user.

In S105, the light source driver 111 drives the light source 109 to emit the light having the wavelength set in S201. In S106, the acoustic image acquired at the data acquisition timing set in S104 is stored in the memory 123. In S202, the controller determines whether the acoustic image is obtained for all wavelength types of the light source set by the user. If not, the flow returns to S201 so as to set the next wavelength of the light source and to resume S105 and S106.

When the acoustic image is obtained for all wavelength types of the light source set by the user, the flow moves to S107. In S107, the controller 112 determines whether the acoustic image acquisition ends for the entire image acquisition area set by the user.

When the acoustic image acquisition does not end, the flow moves to S108 to change the positions of the acoustic lens 102 and the acoustic transducer 101 and obtain the next acoustic image. Then, S102 to S107 are resumed.

When the acoustic image acquisition ends for the user set image acquisition area in S107, the flow moves to S109 to correct the acquired tomogram of the organism 104 by using the magnification $\beta$ calculated in S102. In S110, the tomogram corrected by S109 is output to the output unit 113. Next, the image acquisition ends.

This embodiment uses the acoustic lens 102 to collect the acoustic wave onto the acoustic transducer 101 for photoacoustic imaging of a comparatively deep region in the organism, and may be used with the comparative example.

Second Embodiment

Figure 8:
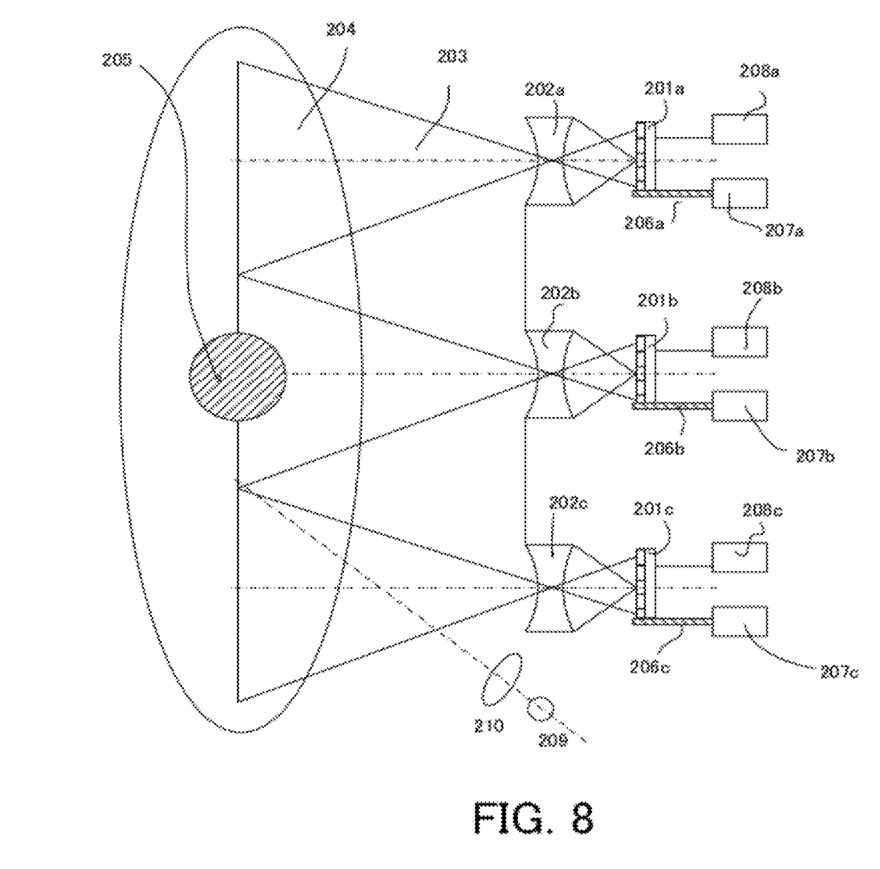
FIG. 8 is a block diagram for explaining a second embodiment of the present invention.

A description will be given of a second embodiment according to the present invention. FIG. 8 is a view for explaining the second embodiment. This embodiment configures the apparatus of the first embodiment to be an array structure, and detects an absorber 205 in an object 204 by using the photoacoustic effect.

Reference numerals 202a, 202b, and 202c denote an array of two-dimensionally arranged acoustic lenses, for which a corresponding one of array type acoustic detectors 201a, 201b, and 201c and a corresponding one of array type drivers 206a, 206b, and 206c are provided. Reference numerals 208a, 208b, and 208c denote acoustic transducer drivers, and reference numerals 207a, 207b, and 207c denote driver controllers.

The principle is similar to that of the first embodiment, and a description thereof will be omitted.

A light source 209 emits pulsed light of the nanosecond order via an illumination optical system 210. The acoustic wave generated from the absorber 205 in the object 204 is detected by the acoustic detectors 201a, 201b, and 201c, and an acoustic image can be obtained in a broad range.

Figure 9:
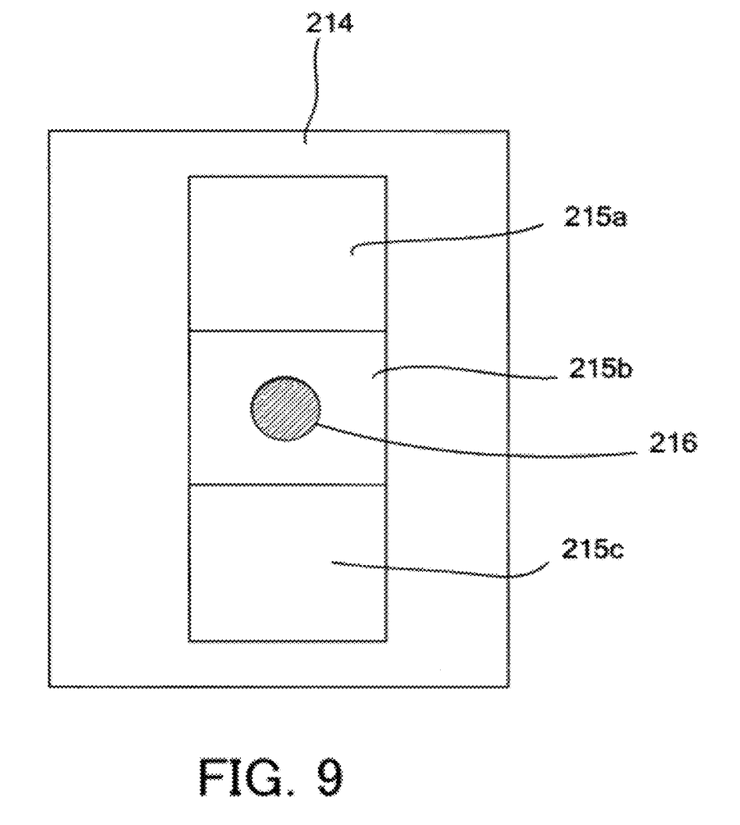
FIG. 9 is a schematic view of an acoustic image obtained in the second embodiment according to the present invention.

FIG. 9 schematically shows the acoustic image. The image obtained from the acoustic detectors 201a, 201b, and 201c are configured to be displayed on areas 215a, 215b, and 215c in a display area 214 in FIG. 9. Reference numeral 216 denotes an image of the absorber 205.

In this embodiment, similar to the first embodiment, the acoustic image can be obtained by changing a focus position and by moving the acoustic detectors 201a, 201b, and 201c using the drivers 206a, 206b, and 206c.

In this embodiment, the position of the light source is set, but not limited, to the position shown in FIG. 8. A plurality of light sources can provide similar effects.

In this embodiment, only the near infrared light is irradiated into the organism from the light source. However, when the wavelength is changed and the photoacoustic method is performed with the photoacoustic wave, a spectral image of the acoustic image can be obtained. The nature of the absorber can be estimated by recognizing the spectral characteristic of the absorber utilizing the spectral information.

Third Embodiment

Figure 11:
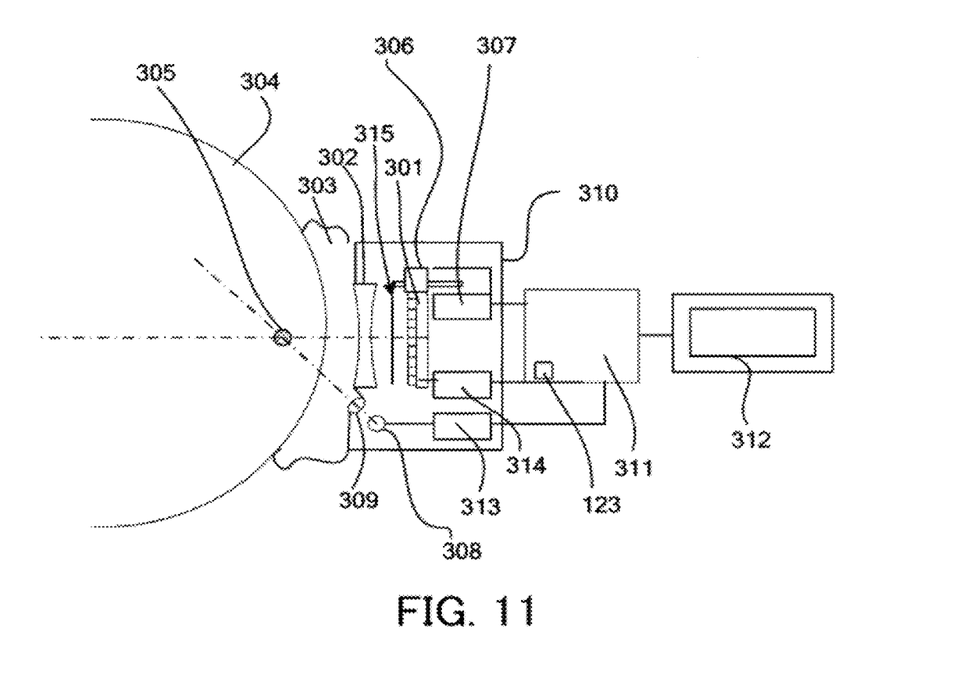
FIG. 11 is a block diagram for explaining a third embodiment according to the present invention.

Referring to FIG. 11, a description will be given of a third embodiment according to the present invention. FIG. 11 shows an illustrative structure of an apparatus configured to obtain the acoustic image utilizing the approach described in the first embodiment.

A housing 310 is a housing configured to house an acoustic transducer 301 and a light source 308, and an observer utilizes the housing 310 and obtains an acoustic image in an object 304 to be measured, which is for example, a human breast. The light does not go straight in the object 304 due to the strong scattering characteristic to the near infrared light although the absorption characteristic is not so strong.

The light source 308 is a light source configured to emit pulsed light of the near infrared light, and connected to a controller 311 via the light source driver 313. The controller 311 has a memory 123, configured to store an acoustic image etc. The light emitted form the light source 308 illuminates the object 304 via the lens 309.

The absorber 305 is located inside of the object 304 exhibits an absorption characteristic to the near infrared light, and generates the acoustic wave when it receives the near infrared light due to the photoacoustic effect. The generated acoustic wave forms an acoustic image on the acoustic transducer 301 via the acoustic lens 302 when the acoustic transducer 301 has a conjugate relationship with the absorber 305 via the acoustic lens 302.

Reference numeral 315 denotes a mechanical shutter, which is provided to the acoustic transducer 301 on the side of the object 304 in this embodiment. The mechanical shutter 315 opens and allows the acoustic wave to pass through it when the acoustic wave is generated from a position conjugate with the acoustic transducer 301 via the acoustic lens 302. However, the mechanical shutter 315 closes and prevents the acoustic waves that are generated from non-conjugate positions from being detected by the acoustic transducer 301.

Of course, a signal processor (not shown) in the above acoustic transducer driver 314 may be used instead of the mechanical shutter 315. The acoustic transducer 301 is connected to the controller 311 via the acoustic transducer driver 314. The driver 306 is connected to the acoustic transducer 301, and configured to change a position of the acoustic transducer 301 relative to the acoustic lens 302. The driver 306 is connected to the controller 311 via the driver controller 307. As an observer (not shown) controls the controller 311, a tomogram can be obtained by sequentially obtaining the acoustic images. The observer can observe the tomogram obtained in the measurements, on the display 312.

This embodiment enables the observer to hold the housing 310, and to use it after the acoustic matching layer (or solution) 303 used for acoustic impedance matching is applied between the object 304 and the acoustic lens 302. The acoustic matching layer 303 can use transparent gel that has ever been used for the acoustic echo device, etc. Alternatively, the matching solution for the acoustic impedance matching may be filled in a space between the acoustic lens 302 and the acoustic transducer 301. This configuration can reduce the acoustic energy loss.

The light source 308 of this embodiment is a light source configured to emit the pulsed light, but may utilize a semiconductor laser, a titanium sapphire laser etc. Spectral imaging can be performed by changing a wavelength variable laser to change the wavelength and by obtaining the acoustic image.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-232174, filed Sep. 10, 2008, which is hereby incorporated by reference herein in its entirety.

What is claimed is:

1. A photoacoustic apparatus comprising:
   an acoustic lens configured to collect an acoustic wave generated by a photoacoustic effect;
   an acoustic detector configured to detect the acoustic wave collected by said acoustic lens; and
   a controller configured to obtain an estimated value of arrival time when the acoustic wave generated from a first position in an object arrives at said acoustic detector based on positions of said acoustic detector and said acoustic lens, to output a first measurement signal resulting from the acoustic wave that is generated from the first position in the object, and to eliminate a second measurement signal resulting from the acoustic wave that is generated from a second position different from the first position in the object based on the estimated value.

2. The photoacoustic apparatus according to claim 1, wherein the first position is conjugate with a position of said acoustic detector with respect to said acoustic lens.

3. The photoacoustic apparatus according to claim 1, wherein said controller eliminates the second measurement signal based on positions of said acoustic detector and said acoustic lens.

4. The photoacoustic apparatus according to claim 1, further comprising a shutter arranged between the object and said acoustic detector,
   wherein opening and closing of said shutter is controlled so as to prevent the acoustic wave generated from the second position from arriving at said acoustic detector and to transmit the acoustic wave generated from the first position to said acoustic detector.

5. The photoacoustic apparatus according to claim 1, wherein said acoustic detector detects both the acoustic wave generated from the first position and the acoustic wave generated from the second position, and
   wherein said controller provides a process that eliminates the second measurement signal based on the acoustic wave generated from the second position based on a detection result provided by said acoustic detector.

6. The photoacoustic apparatus according to claim 1, further comprising a light source to illuminate the object and a unit configured to change a wavelength of light generated by said light source.

7. The photoacoustic apparatus according to claim 1, further having an impedance matching solution between said acoustic lens and said acoustic detector.

8. The photoacoustic apparatus according to claim 1, further comprising a driver configured to move at least one of said acoustic detector and said acoustic lens.

9. The photoacoustic apparatus according to claim 8, wherein said acoustic lens includes an array of two-dimensionally arranged acoustic lenses, and
   wherein the photoacoustic apparatus includes a plurality of said acoustic detectors and a plurality of said drivers, both the number of acoustic detectors and the number of drivers being equal to the number of acoustic lenses.

10. A photoacoustic apparatus comprising:
    an acoustic lens configured to collect an acoustic wave generated by a photoacoustic effect;
    an acoustic detector configured to detect the acoustic wave collected by said acoustic lens;
    a controller configured to output a first measurement signal resulting from the acoustic wave that is generated from a first position in an object, and to eliminate a second measurement signal resulting from the acoustic wave that is generated from a second position different from the first position in the object; and
    a shutter arranged between the object and said acoustic detector,
    said controller configured to control opening and closing of said shutter so as to transmit the acoustic wave generated from the first position in the object to said acoustic detector, and to prevent the acoustic wave generated from the second position different from the first portion in the object from arriving at said acoustic detector.

11. The photoacoustic apparatus according to claim 10, wherein the first position is conjugate with a position of said acoustic detector with respect to said acoustic lens.

12. The photoacoustic apparatus according to claim 10, wherein said controller eliminates the second measurement signal based on positions of said acoustic detector and said acoustic lens.

13. The photoacoustic apparatus according to claim 10, wherein said acoustic detector detects both the acoustic wave generated from the first position and the acoustic wave generated from the second position, and
    wherein said controller provides a process that eliminates the second measurement signal based on the acoustic wave generated from the second position based on a detection result provided by said acoustic detector.

14. The photoacoustic apparatus according to claim 10, further comprising a light source to illuminate the object and a unit configured to change a wavelength of light generated by said light source.

15. The photoacoustic apparatus according to claim 10, further having an impedance matching solution between said acoustic lens and said acoustic detector.

16. The photoacoustic apparatus according to claim 10, further comprising a driver configured to move at least one of said acoustic detector and said acoustic lens.

17. The photoacoustic apparatus according to claim 16, wherein said acoustic lens includes an array of two-dimensionally arranged acoustic lenses, and
    wherein the photoacoustic apparatus includes a plurality of said acoustic detectors and a plurality of said drivers, both the number of acoustic detectors and the number of drivers being equal to the number of acoustic lenses.

* * * * *